US00PP37025P2

(12) United States Plant Patent
Yam

(10) Patent No.: US PP37,025 P2
(45) Date of Patent: Oct. 14, 2025

(54) ***EPIPREMNUM* PLANT NAMED 'Sao Paulo'**

(50) Latin Name: *Epipremnum*
Varietal Denomination: Sao Paulo

(71) Applicant: Tai Yam, Apopka, FL (US)

(72) Inventor: Tai Yam, Apopka, FL (US)

( * ) Notice: Subject to any disclaimer, the term of this patent is extended or adjusted under 35 U.S.C. 154(b) by 0 days.

(21) Appl. No.: 18/991,821

(22) Filed: Dec. 23, 2024

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell

(57) ABSTRACT

A new and distinct cultivar of *Epipremnum* aureum plant named 'Sao Paulo' is disclosed, characterized by a uniquely rugose leaf texture and interesting color pattern. The upper leaf surface has distinct wrinkling/rugosity, along with darker translucent ripple patterns. The under surface of the foliage has rippled markings. Leaf lamina is thicker than typical for *Epipremnum.* Plants have a more upright habit, both unique and atypical for the Genus. The new variety is an *Epipremnum* typically produced as an indoor ornamental plant.

2 Drawing Sheets

Figure 1:
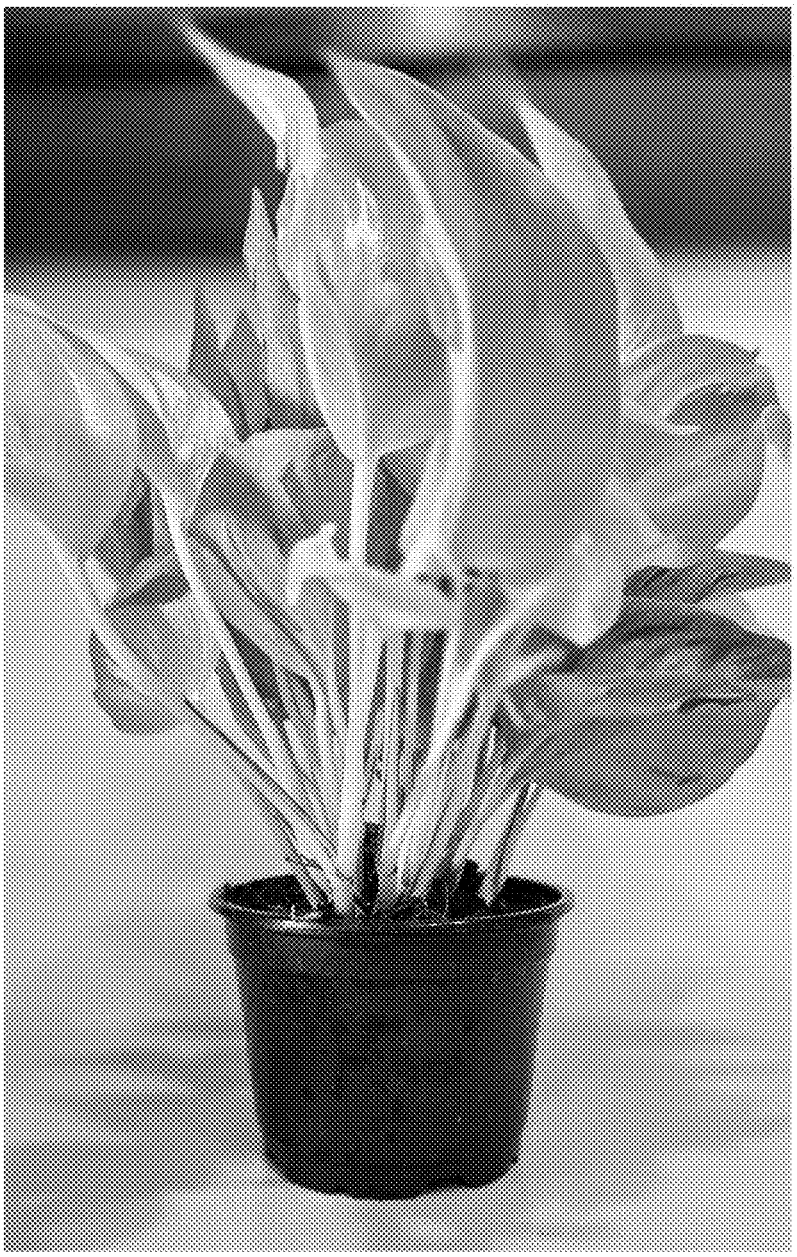

Latin name of the genus and species: *Epipremnum aureum.*

Variety denomination: 'Sao Paulo'.

BACKGROUND OF THE INVENTION

The new cultivar is a product of chance discovery by the inventor Tai Yam. The new variety 'Sao Paulo' was discovered as a naturally occurring, whole plant mutation at a commercial nursery in Thanyaburi District, Pathum Thani, Thailand during October of 2023. The interesting mutation was identified in a commercial mother stock planting of *Epipremnum aureum* 'Neon', unpatented.

Asexual reproduction of the new cultivar 'Sao Paulo' was first performed at a commercial nursery in Thanyaburi District, Pathum Thani, Thailand by vegetative cuttings in October of 2023. Plants were tested and evaluated to determine the stability of the novel characteristics of the new variety. Asexual propagation has shown that the unique features of this cultivar are stable and reproduced true to type in multiple successive generations.

SUMMARY OF THE INVENTION

The cultivar 'Sao Paulo' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Sao Paulo'. These characteristics in combination distinguish 'Sao Paulo' as a new and distinct *Epipremnum* cultivar:

1. Unique leaf texture; the underside of the leaves consistently displays rippled markings.
2. Rugose leaf surface; the upper leaf surface has distinct wrinkling/rugosity, along with darker translucent ripple patterns.

3. Thicker leaves; the leaf lamina is significantly thicker than that of the parent 'Neon'.
4. Novel undulation to leaf.
5. Upright growth habit in the first 2 months; plants grow upright initially, giving the appearance of a light green flame; most *Epipremnums* are trailing.

PARENT COMPARISON

Plants of the new cultivar 'Sao Paulo' are similar to the parent *Epipremnum aureum* 'Neon' in most horticultural characteristics. The new variety however differs in the following characteristics:

1. *Epipremnum* 'Sao Paulo' has an upright growth habit in the first 2 months; 'Neon' has a trailing habit all though its growth cycle.
2. *Epipremnum* 'Sao Paulo' grows more slowly than *Epipremnum* 'Neon'.
3. *Epipremnum* 'Sao Paulo' has an improved adaptation to low light conditions than *Epipremnum* 'Neon'.

COMMERCIAL COMPARISON

Plants of the new cultivar 'Sao Paulo' are similar to the commercial variety *Epipremnum aureum* 'Jessenia', unpatented in most horticultural characteristics. The new variety however differs in the following characteristics:

1. *Epipremnum* 'Sao Paulo' has an upright growth habit in the first 2 months; 'Jessenia' has a trailing habit all through its growth cycle.
2. *Epipremnum* 'Sao Paulo' produces leaf rugosity not found on *Epipremnum* 'Jessenia'.
3. *Epipremnum* 'Sao Paulo' has a thicker leaf than *Epipremnum* 'Jessenia'.

BRIEF DESCRIPTION OF THE PHOTOGRAPHS

The accompanying photograph in FIG. 1 illustrates in full color a typical plant of 'Sao Paulo' grown in a greenhouse in Thanyaburi District, Pathum Thani, Thailand. This plant is approximately 18 weeks old, shown in a 10 cm pot.

Figure 2:
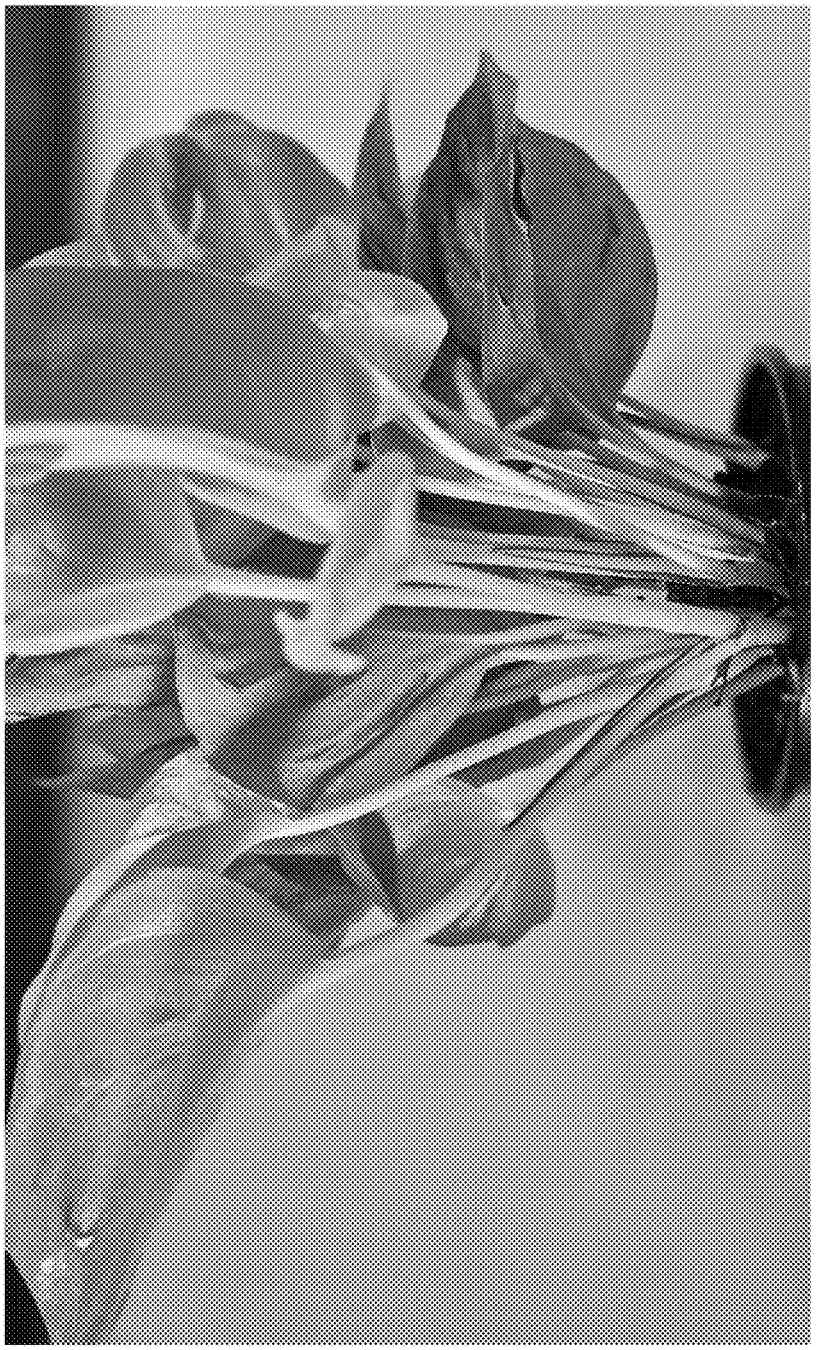

FIG. 2 illustrates a closer view of the underside of the foliage of the same plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'Sao Paulo' plants grown in a greenhouse in Thanyaburi District, Pathum Thani, Thailand. Temperatures ranged from 30° C. to 35° C. during the day, 18° C. to 25° C. at night. Plants were grown in 30% to 50% shade. No artificial light, photoperiodic treatments were given to the plants. Measurements and numerical values represent averages of typical plant types.

Botanical classification: *Epipremnum aureum* 'Sao Paulo'.

Age of plant described: 18 weeks from a rooted cutting.

PROPAGATION AND PRODUCTION

Type of propagation typically used: Terminal vegetative cuttings.

Time to initiate rooting: About 2 weeks at approximately 25 to 30° C.

Time to produce a rooted plantlet: About 3 weeks at approximately 22° C. to 28° C.

Root description: Fleshy moderately dense roots. White 155D and Orange-White 159C in color.

PLANT

Growth habit: Compact, growth. Basal leaves emerge in clumps.

Pot size of plant described: 10 cm.

Normal commercial pot sizes: 10, 12, 15, to 20 cm pots.

Plant shape: Inverted triangle in first 2 months. With maturity either trailing or climbing plant with a globose center.

Height: Approximately 28 cm.

Plant spread: Approximately 30 cm.

Growth rate: Moderate. Approximately 5 cm per month.

Branching characteristics: Moderate branching habit. Less branching than typical of species. Side shoots and branches produced over time, especially when pruned or encouraged to climb a support. An 18 week old plant has about 10 lateral branches.

Diameter of stem: Approximately 5 cm.

Length of stem: 10 to 20 cm at 18 weeks.

Shape of stem: Round.

Texture of stem: Smooth and slightly glossy.

Color of stem: Yellow-Green 149D.

Stem strength: As the plant matures, the stems tend to become thicker and slightly more rigid, offering increased support.

FOLIAGE

Leaf:

*Arrangement*.—Sub-alternate, occurring only top surfaces of branch.

*Average length*.—Approximately 8.5 cm.

*Average width*.—Approximately 7.5 cm.

*Shape of blade*.—Heart-shaped.

*Aspect*.—Undulating.

*Apex*.—Acute or apiculate.

*Base*.—Rounded to nearly cordate.

*Margin*.—Entire.

*Texture of top surface*.—Wrinkles and darker, translucent ripple patterns.

*Texture of bottom surface*.—Consistent ripple markings.

*Color*.—Young foliage upper side: Near R.H.S. Yellow-Green 149C. Young foliage under side: Near R.H.S. Yellow-Green 149C, often variegated with Yellow-Green N144B. Mature foliage upper side: Near R.H.S. Yellow-Green 149A, often variegated with Yellow-Green 144C and Yellow-Green N144B. Mature foliage under side: Near R.H.S. Yellow-Green 149A, often variegated with Yellow-Green 144C and Yellow-Green N144B.

*Venation*.—Type: Reticulate venation. Color: Light to Medium Green. Upper side: Yellow-Green 149A. Underside: Yellow-Green 149D.

Petiole:

*Length*.—Average range 3.5 to 4.5 cm.

*Width*.—Approximately 5 mm.

*Texture*.—Glabrous.

*Color*.—Upper side: Yellow-Green 149C. Underside: Yellow-Green 149D.

*Strength*.—Moderate, flexible, not easily broken.

Sheath (if present):

*Average length*.—Approximately 2.5 cm.

*Average width*.—Approximately 1 cm.

*Color*.—Yellow-Green 149D.

FLOWERS

Not observed to date and not typically producing flowers.

OTHER CHARACTERISTICS

Disease and pest resistance: Typical resistance and susceptibility to normal pests and diseases of *Epipremnum* has been observed. Typical diseases found in the Marantaceae family include: *Pseudomonas* species, *Pseudomonas cichorii, Alternaria alternata, Fusarium oxysporum.* Typical pests include: *Radopholus similis, Tetranychus urticae,* and various flies from the *Sciaridae* family.

Drought Tolerance and Temperature Tolerance: Moderate drought tolerance. Plants can withstand periods of dryness, making it a relatively low-maintenance plant. However, it's important to avoid prolonged drought, as this can lead to leaf drop and overall plant stress. Plants thrive in average room temperatures between 55° F. and 85° F. They can tolerate slightly lower temperatures, but prolonged exposure to cold can damage the plant.

Fruit/seed production: Not observed.

What is claimed is:

1. A new and distinct cultivar of *Epipremnum* plant named 'Sao Paulo' as herein illustrated and described.

* * * * *